United States Patent
Heidenau

(10) Patent No.: US 12,414,904 B2
(45) Date of Patent: Sep. 16, 2025

(54) COMPOSITION FOR THE REMINERALIZATION OF TEETH

(71) Applicant: Ferton Holding S.A., Delémont (CH)

(72) Inventor: Frank Heidenau, Pegnitz (DE)

(73) Assignee: Ferton Holding S.A., Delémont (CH)

( * ) Notice: Subject to any disclaimer, the term of this patent is extended or adjusted under 35 U.S.C. 154(b) by 701 days.

(21) Appl. No.: 17/624,664

(22) PCT Filed: Jul. 3, 2020

(86) PCT No.: PCT/EP2020/068810
§ 371 (c)(1),
(2) Date: Jan. 4, 2022

(87) PCT Pub. No.: WO2021/001529
PCT Pub. Date: Jan. 7, 2021

(65) Prior Publication Data
US 2022/0273522 A1    Sep. 1, 2022

(30) Foreign Application Priority Data
Jul. 4, 2019    (EP) .................................... 19184355

(51) Int. Cl.
| | |
|---|---|
| *A61K 6/838* | (2020.01) |
| *A61K 6/20* | (2020.01) |
| *A61K 8/24* | (2006.01) |
| *A61K 8/25* | (2006.01) |
| *A61Q 11/00* | (2006.01) |
| *C03C 3/16* | (2006.01) |
| *C03C 4/00* | (2006.01) |

(52) U.S. Cl.
CPC ................ *A61K 6/838* (2020.01); *A61K 6/20* (2020.01); *A61K 8/24* (2013.01); *A61K 8/25* (2013.01); *A61Q 11/00* (2013.01); *C03C 3/16* (2013.01); *C03C 4/0021* (2013.01); *C03C 2205/06* (2013.01)

(58) Field of Classification Search
None
See application file for complete search history.

(56) References Cited

U.S. PATENT DOCUMENTS

| | | | |
|---|---|---|---|
| 5,037,639 A | 8/1991 | Tung | |
| 7,906,132 B2 | 3/2011 | Ziegler et al. | |
| 8,609,071 B2 * | 12/2013 | Reynolds | C07K 7/06 424/52 |

(Continued)

FOREIGN PATENT DOCUMENTS

| | | |
|---|---|---|
| AU | 2020300821 A1 | 1/2022 |
| CA | 3144016 A1 | 1/2021 |

(Continued)

OTHER PUBLICATIONS

Office Action corresponding to Chinese Application No. 202080049060.6 dated Jun. 10, 2023 with translation.

(Continued)

*Primary Examiner* — Michael Forrest
(74) *Attorney, Agent, or Firm* — Jenkins, Taylor & Hunt, P.A.

(57) ABSTRACT

The present invention relates to a composition for the remineralization of teeth and to the use thereof. The composition comprises calcium phosphate (CaP) glass, and aqueous silica sol.

7 Claims, 3 Drawing Sheets

(56) References Cited

U.S. PATENT DOCUMENTS

| | | | |
|---|---|---|---|
| 8,957,126 B2* | 2/2015 | Rusin | A61K 6/836 |
| | | | 106/35 |
| 9,034,301 B2 | 5/2015 | Sakuma et al. | |
| 9,402,933 B2 | 8/2016 | Heidenau et al. | |
| 2003/0124066 A1 | 7/2003 | Dixon, Jr. et al. | |
| 2010/0086497 A1 | 4/2010 | Burwell et al. | |
| 2017/0319455 A1 | 11/2017 | Farooq et al. | |

FOREIGN PATENT DOCUMENTS

| CN | 101102741 A | 1/2008 |
|---|---|---|
| CN | 102245153 A | 11/2011 |
| CN | 114080209 A | 2/2022 |
| EP | 1 811 942 | 11/2001 |
| EP | 1 343 450 | 9/2003 |
| EP | 3966175 A1 | 3/2022 |
| JP | S6172638 A | 4/1986 |
| JP | S6310039 | 1/1988 |
| JP | H08245353 A | 9/1996 |
| JP | 2008521754 A | 6/2008 |
| JP | 2008543887 A | 12/2008 |
| JP | 2011037779 A | 2/2011 |
| JP | 2017178912 A | 10/2017 |
| JP | 2022538675 A | 9/2022 |
| WO | WO 2002/049578 | 6/2002 |
| WO | WO 2006/055317 | 5/2006 |
| WO | WO2006/056013 A1 | 6/2006 |
| WO | WO2006/135982 A1 | 12/2006 |
| WO | WO2008/126410 A1 | 10/2008 |
| WO | WO 2019/034348 | 2/2019 |
| WO | WO 2019/068596 | 4/2019 |
| WO | WO 2010/041073 | 4/2020 |
| WO | WO2021/001529 A1 | 1/2021 |

OTHER PUBLICATIONS

Translation of the Written Opinion of the International Searching Authority corresponding to International Patent Application PCT/EP2020/068810 dated Jan. 7, 2021.
International Preliminary Report on Patentability corresponding to International application No. PCT/EP 2020/068810 dated Dec. 28, 2021.
International Search Report corresponding to International Patent Application No. PCT/EP2020/068810 dated Oct. 12, 2020.
Rao et al., "Optical and Mechanical Properties of Calcium Phosphate Glasses," Glass Physics and Chemistry, vol. 40, No. 3, pp. 303-309 (2014).
Kasuga, "Coatings for metallic biomaterials," Metals for Biomedical Devices, Woodhead Publishing Series in Biomaterials, pp. 260-282 (2010).
Elliott, "Chapter 1—General Chemistry of the Calcium Orthophosphates, 1.8 Amorphous Calcium Phosphates," Studies in Inorganic Chemistry, vol. 18, pp. 1-62 (1994).
Venkateswara, et al. (2014) "Optical and Mechanical Properties of Calcium Phosphate Glasses," Glass Physics and Chmistry, vol. 40, No. 3; pp. 303-309.
Office Action and search received in Japanese Patent Application No. 2021578266 mailed on Feb. 16, 2024, 22 pages. (Translation).
Office Action received in Canadian Patent Application No. 3,144,016 mailed on Jun. 3, 2025, 5 pages.
Examination Report No. 1 received in Australian Patent Application No. 2020300821 mailed on Aug. 11, 2025, 4 pages.

* cited by examiner

COMPOSITION FOR THE REMINERALIZATION OF TEETH

The present invention relates to a composition for remineralizing teeth and to the use thereof. The composition comprises calcium phosphate (CaP) glass and aqueous silica sol.

BACKGROUND OF THE INVENTION

Calcium phosphate is one of the most useful materials in the skeleton: as the principal constituent of teeth and bone, it provides hardness and stability. Remineralization (reincorporation of minerals) in teeth therefore increases their hardness and resistance to caries.

There are numerous compositions known in the prior art for the remineralization of teeth.

WO 2010/041073 A1, for example, describes a film for use in the oral cavity, the film comprising the following: a water-soluble polymeric film former; and a bioactive glass; the film being capable of adhering to at least one tooth in the oral cavity for a maximum time of about 60 minutes before the film disintegrates or substantially disintegrates, and the film being capable of carrying out remineralization of the tooth. For example, the film comprises a water-soluble polymeric film former selected from methylcellulose, hydroxypropylmethylcellulose, hydroxyethylcellulose, hydroxypropylcellulose and carboxymethylcellulose; and a bioactive glass which comprises silicon dioxide, sodium oxide, calcium oxide and phosphorus oxide.

EP 1 343 450 relates to a dental adhesive film for the local treatment of teeth by remineralization. This film consists of a carrier material, which adheres to the teeth and is soluble or swellable in water, and of active ingredients stored in this material. An active ingredient in the film is a finely divided calcium salt of low solubility in water, selected from the group of phosphates, fluorides, fluorophosphates and mixtures thereof, preferably hydroxylapatite and/or fluoroapatite, having a mean particle size of between 10 and 300 nm. Furthermore, the carrier material preferably comprises a protein component, preferably in the form of a composite material consisting of a calcium salt with low solubility in water and in protein components.

EP 1 811 942 describes a dental composition comprising: an ethylenically unsaturated compound with acid functionality; an ethylenically unsaturated compound without acid functionality; and a glass which releases calcium and phosphorus, the acid functionality comprising a phosphoric acid functionality.

WO 2019/068596 relates to a dental cleansing composition comprising spherical, anhydrous, amorphous silica gel particles with a pore volume of less than 0.1 ml/g, and an orally compatible carrier.

WO 2019/034348 discloses an oral care composition which comprises a bioactive glass, a calcium source soluble and/or weakly soluble in water, a phosphate source, and a physiologically acceptable carrier, where the bioactive glass and the readily soluble and/or water-soluble calcium source are present in a weight ratio (a:b) of 1:3 to 20:1, and where the calcium source is calcium chloride, calcium nitrate, calcium gluconate, calcium glycerophosphate or mixtures thereof.

SUMMARY OF THE INVENTION

It is an object of the present invention to provide a composition which fully protects the dentin surfaces of the teeth and significantly minimizes unevennesses and defects on the dentin surfaces.

The present invention relates to a composition for remineralizing teeth, comprising or consisting of:
a) calcium phosphate (CaP) glass, and
b) aqueous silica sol.

The composition of the present invention is preferably free from $SiO_2$ as a glass constituent.

DETAILED DESCRIPTION OF THE INVENTION

As described above, the composition of the invention for remineralizing teeth comprises a) calcium phosphate (CaP) glass, and b) aqueous silica sol.

In one embodiment the composition consists only of these two constituents.

The composition of the invention serves for use in the mineralization of teeth. The composition is applied to the tooth necks in the gum pocket using an instrument (e.g., cotton bud, brush, airflow). In this case a gel layer ($SiO_2$) is formed, comprising ultrafine glass particles (calcium phosphate glass). This gel layer cures and initially provides surface sealing of the exposed dentinal tubules in the tooth neck.

In the subsequent days, the calcium phosphate glass is disintegrated in the oral environment and from its ionic constituents, hydroxyl apatite or calcium phosphate is formed with remineralization in the open dentinal tubules. As a result, these tubules are permanently sealed As a result, the sensitivity of the teeth to hot/cold or sweet/sour is reduced and periodontal disease is halted. There is also soothing of the gum pockets in the oral mucosa, and in the best case reformation of the gum pocket damaged by periodontal disease.

A silica sol as used herein is preferably an aqueous colloidal suspension of virtually spherical molecules of polysilicic acid, containing 10% to a maximum of 90% by mass, preferably 15-50% by mass, of silicon dioxide (the remainder being water). One example of the aqueous silica sol used in the invention is the product marketed under the name KÖSTROSOL® and manufactured by Chemiewerk Bad Köstritz GmbH. This product may be defined chemically as an aqueous, colloidal, weakly alkaline silica dispersion. The constituents of the composition are as follows:

| Components | CAS No. | EINECS No. | % by mass |
|---|---|---|---|
| Amorphous silica | 7631-86-9 | 231-545-4 | 15-50 |
| Water | 7732-18-5 | 231-791-2 | 44.5-84.5 |

The CaP glass is preferably ground and sieved, and has a particle size <100 μm. In one preferred embodiment the particle size of the CaP glass has a $D_{50}$<35, preferably <20, or <10 μm and/or a $D_{90}$<90, preferably <20 μm.

The particle size is determined preferably via a sieve analysis (sieving tower, for example), the particle size distribution being based on the mass. This means that in the case, for example, of a $D_{50}$=10 μm, a 50% mass fraction of the particles in a given sample have a size <10 μm and 50% mass fraction of the particles have a size >10 μm. In analogy, in the case of a $D_{90}$=20 μm, the mass fraction of the particles in a given sample having a size <20 μm would be 90%, and the mass fraction of the particles having a size >90 μm would be 10%.

The sieve analysis is described in German Standard DIN 66165, for example. The standard consists of two parts; DIN 66165-1 defines the principles, DIN 66165-2 the procedure for the sieve analysis.

The composition of the invention further additionally comprises preferably fully demineralized water and/or dilute hydrochloric acid. The fully demineralized water is preferably boiled for sterilization. In this case the preferred constituents of the composition of the invention are calcium phosphate (CaP) glass, aqueous silica sol, fully demineralized water and dilute hydrochloric acid (for pH adjustment). The dilute hydrochloric acid may be prepared from 1.62 g of 35% hydrochloric acid per 100 g of FD water. The preferred pH of the composition is approximately pH 6.6-6.7.

In another embodiment, the composition of the invention further comprises chlorhexidine digluconate and/or dilute hydrochloric acid.

Chlorhexidine digluconate is used generally for the prevention and treatment of infectious diseases, as in the case of small wounds and injuries, for example, in the case of mild burns, and also in gum inflammation and other inflammatory and infectious diseases of the mouth and throat. The actual active constituent is chlorhexidine, an active antiseptic ingredient from the group of disinfectants, which is employed for preventing and treating infectious diseases and for oral hygiene. The chlorinated biguanide derivative is active in particular against bacteria. The effects derive from a disruption to the function of the cell membrane.

Chlorhexidine digluconate is added to the composition in pharmaceutically customary amounts (0.1-0.2% w/w).

The calcium phosphate (CaP) glass used in the invention is produced preferably from approximately equimolar amounts of $CaCO_3$ and $P_2O_5$. A precise preparation example for the calcium phosphate glass of the invention is found in the working examples which follow.

In one preferred embodiment the composition of the invention for remineralizing teeth comprises the following constituents: approximately $SiO_2$ sol 26-27% w/w, water 53-54% w/w, and CaP glass 19-21% w/w, based on the total amount of the $SiO_2$ sol, water and CaP glass constituents.

Alternatively the composition of the invention for remineralizing teeth comprises the following constituents: approximately $SiO_2$ sol 30-35% w/w, water 60-70% w/w, and CaP glass 2-3% w/w, based on the total amount of the $SiO_2$ sol, water and CaP glass constituents.

In addition there is optionally a small amount of dilute HCl for pH adjustment, and/or chlorhexidine digluconate.

The pH of the composition is preferably approximately pH 6.6-6.7

The composition comprises, for example, the following proportions of the constituents in the dry matter:
 mass fraction of Ca in the dry matter: 20.4% by mass
 mass fraction of P in the dry matter: 31.2% by mass
 mass fraction of Si in the liquid component (Köstrosol): 4.67% by mass
 mass fraction of Si in the total mixture: 4.55% by mass According to a further aspect of the present invention, the composition outlined above is used for remineralizing teeth. As already outlined above, the composition is applied to the tooth necks in the gum pockets with an instrument. In this case a gel layer ($SiO_2$) is formed which comprises ultrafine glass particles (calcium phosphate glass). This gel layer cures and initially provides a surface sealing of the exposed dentinal tubules in the tooth neck. In the subsequent days, the calcium phosphate glass is disintegrated in the oral environment, and hydroxyl apatite or calcium phosphate is formed from its ionic constituents with remineralization in the open dentinal tubules.

EXAMPLES

1 Production of Calcium Phosphate Glass
1.1 Production of Raw Glass Mixture

Producing a crucible charge of the calcium phosphate glass requires 101.09 g of $CaCO_3$ (1.00 mol) and 141.94 g of $P_2O_5$ (1.00 mol).

25.27 g of $CaCO_3$ (0.250 mol) are weighed out and placed in an agate mortar. Then, using a ceramic spatula, 35.48 g of $P_2O_5$ (0.250 mol; NB: highly hygroscopic!) are weighed out rapidly and added to the $CaCO_3$ in the agate mortar.

The mixture undergoes intimate trituration for 2 minutes. The mixture must then rest for 5 minutes, and is then triturated again for 2 minutes.

The mixture is introduced into the aluminum oxide crucible, and a further portion is prepared as described above from 25.27 g of $CaCO_3$ and 35.48 g of $P_2O_5$, and so on. Owing to the capacity of the agate mortar, larger amounts must not be triturated at once, in order to ensure effective mixing.

1.2 Preparation of the Firing Oven (Glass Melting)

Figure 1:
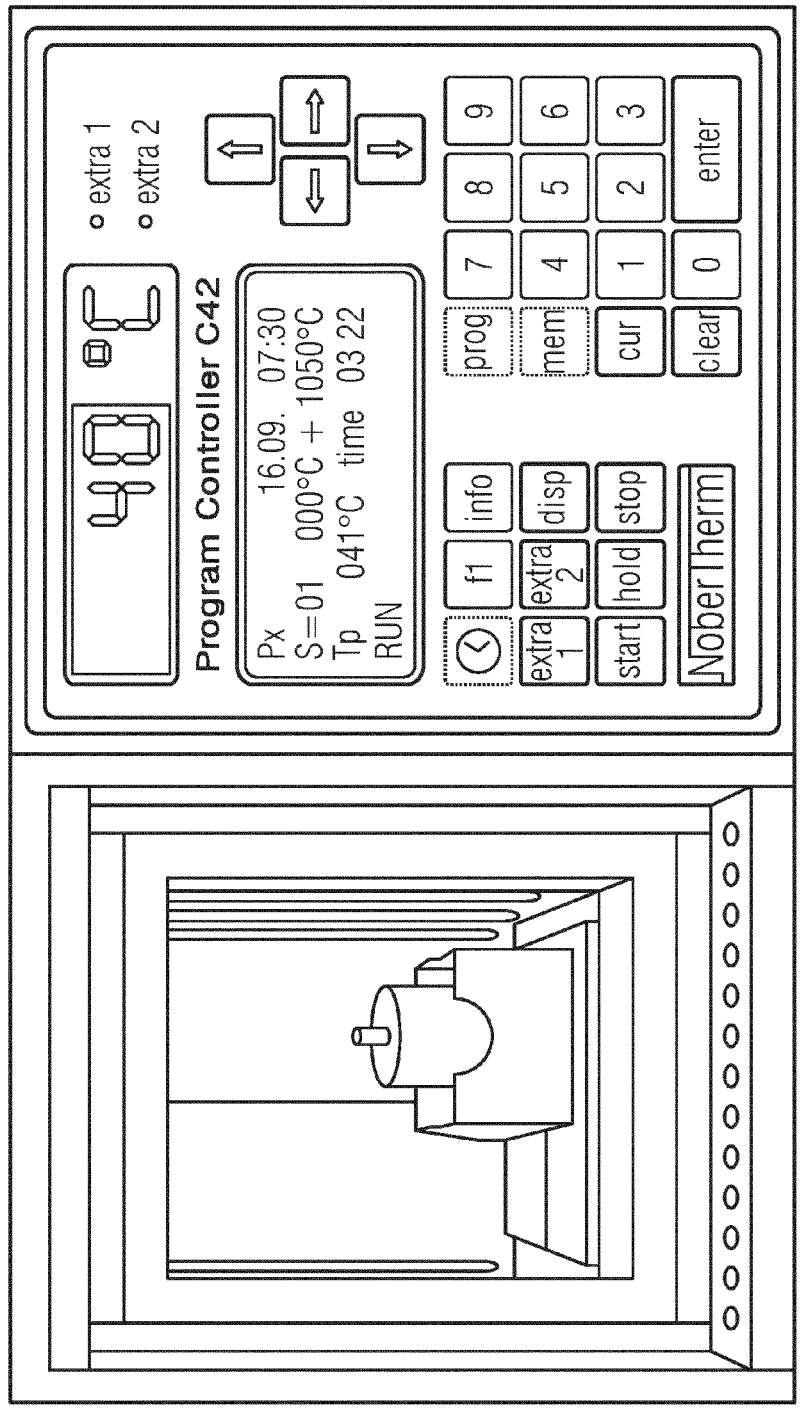
FIG. 1: left) oven charge; right) oven programming.

The oven is charged as shown in FIG. 1. The oven is closed and the sintering program is selected with a heating rate of 0° C.-1050° C.: 300 K/h.

See FIG. 1: left) oven charging; right) oven programming.

1.3 Glass Casting

A heat-resistant pail must be provided with cold mains water (not FD water, to prevent leaching of the glass!).

The crucible is grasped with the tongs (verify secure grip), moved to a short way above the pail (avoid splashing), and the glass melt is poured into the cold water. The operation must be carried out safely but rapidly in order to prevent the glass melt cooling in the crucible.

Thereafter, the crucible is to be placed back into the ceramic housing in the oven, the oven sealed, and allowed to cool down freely.

The solidified glass should be removed from the water as soon as possible and dried in a drying cabinet at 40° C. for 16 hours. After that it can be ground.

1.4 Glass Grinding

The solidified glass should be roughly comminuted and then divided between two aluminum oxide grinding cups. Aluminum oxide grinding beads (3 medium beads d=1.5 cm, 4 small beads, d=1 cm) are added and the glass is ground in the planetary ball mill at 200 rpm for 4 hours. In order to ensure that no relatively large particles are left (there may be glass splinters and relatively large grains!), the ground glass is sieved with a sieve (200 μm) in the sieving tower. For determination of the mean particle size, a sample is taken and subjected to measurement by laser granulometer ($D_{50}$<25 μm).

2 Production of the Mixture Components 2.1 Chemicals

Köstrosol® 0830 (aqueous silica sol, see "Köstrosol 830 data sheet")

fully demineralized water (FD water), boiled for sterilization dilute hydrochloric acid (1.62 g of 35% hydrochloric acid to 100 g of FD water)

calcium phosphate glass (ground and sieved; particle size <100 μm, see section 1)

Chlorhexidine digluconate 20% (optional)

2.2 Apparatus

Sartorius CP324S analytical balance

Brand Transferpette S (volume 500-5000 μl)

Brand Transferpette S (volume 100-1000 μl)

Portamess 911 pH pH meter (from Knick)

150 ml beakers (for preparing the liquid component)

1 small rolled-edge glass vessel (for weighing out calcium phosphate glass)

12 rolled-edge glass vessels (50 mm×20 mm, 15 ml capacity) for the application units 12 fitting lids 12 magnetic stirring rods (10×6 mm)

Multipoint stirrer (from. VarioMag)

Beakers, rolled-edge glass vessels and magnetic stirring rods are sterilized by boiling in fully demineralized water (FD water). The lids are disinfected with Bacillol® (cleaning product based on 2-propanol, 1-propanol and ethanol).

2.3 Preparation of Liquid Component 26.8 g of Köstrosol® and 53.2 g of boiled water are weighed out. The two components are then combined and stirred for around 15 minutes.

2.4 Preparation of Suspensions

For each application unit, 5 g of the liquid component are used. Weighing takes place on the Sartorius CP324S analytical balance. In each case 4710 μl of the liquid component (density: 1.06 g/ml) are pipetted using the Brand Transferpette S (volume 500-5000 μl) into the 12 rolled-edge glass vessels. Subsequently in each case 0.125 g of the solid component (calcium phosphate glass) are weighed out into a small rolled-edge glass vessel on the Sartorius CP324S analytical balance and transferred into the 12 rolled-edge glass vessels containing the liquid component.

Suspensions are formed by combining liquid and solid components. The rolled-edge glass vessels are sealed with the associated lids. The samples are subsequently stirred on the multipoint stirrer (from VarioMag) at 700-750 rpm for around 1 hour.

2.5 pH Measurement and HCl Addition

After a stirring time of 1 hour, 300 μl of dilute hydrochloric acid in each case are added using the Brand Transferpette S (volume 100-1000 μl). The 12 rolled-edge glass vessels are then sealed again. The samples are stirred overnight.

2.6 Addition of Chlorhexidine Digluconate (20%)

Lastly, chlorhexidine digluconate (20%) is added. It is weighed out on the Sartorius CP324S analytical balance. 50 μl of chlorhexidine digluconate (20%) in each case are transferred using the Brand Transferpette S (volume 100-1000 μl) into the 12 samples. The individual weighed amounts are recorded. Following the addition of chlorhexidine digluconate, the samples are sealed again and stirred further for 5 minutes more. A flocky precipitate is formed. On prolonged standing (around 2 hours) the sample become solid.

3 Sealing of Dentinal Tubules in an In Vitro Experiment 3.1 Sample Preparation

Tooth samples were polished transversely to the dentinal tubules. Remineralization suspension was applied using cotton buds to the cleaned and dried samples. The suspension acted on the tooth (dentin) for 10 minutes. The samples were subsequently stored for defined times (0 d, 1 d, 7 d, 14 d) in saline solution (medium was changed daily). This setup served to simulate the environment in the oral cavity. At the observation times, the samples were removed, dried and analyzed by scanning electron microscopy (SEM).

3.2 Experimental Results

Figure 2:
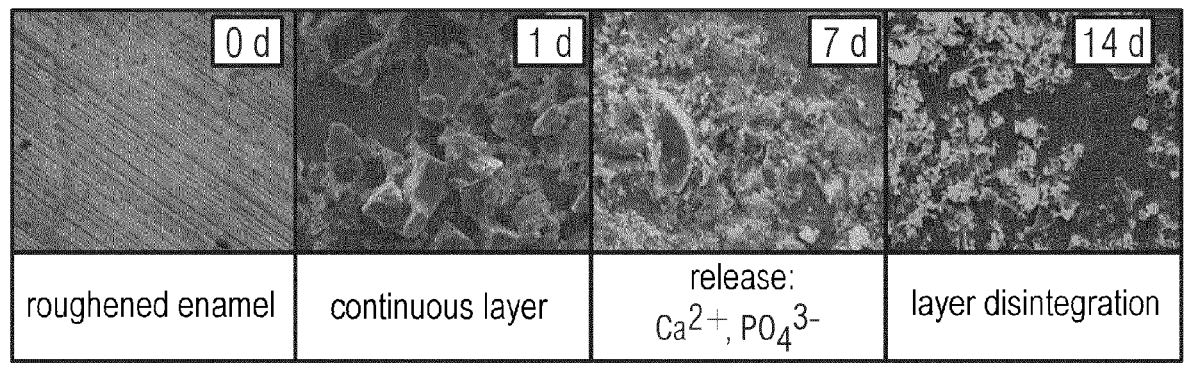
FIG. 2: SEM images (magnification 2500) of treated dentin surfaces after 0 d, 1 d, 7 d and 14 d.

The SEM images in FIG. 2 show the treated dentin surfaces at the various observation times (0 d, 1 d, 7 d, 14 d).

See FIG. 2: SEM images (magnification 2500) of treated dentin surfaces after 0 d, 1 d, 7 d and 14d.

At time 0 d, only roughened enamel is present. Thereafter the bioglass-based remineralizing paste identified in the use example is applied. After 1 d a continuous layer is still perceivable. After 7 d the coating beings to disintegrate, and release of calcium ions and phosphate ions commences. These ions remineralize to form calcium phosphate and seal the dentinal tubules under the coating, by exceeding the solubility product of calcium and phosphate.

Figure 3:
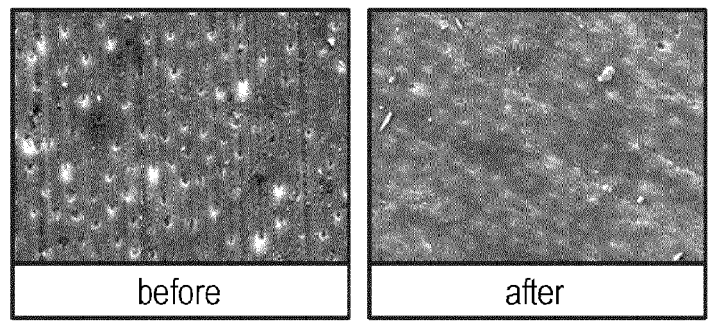
FIG. 3: Dentin surfaces with vertical dentinal tubules before (0 d) and after (14 d) the treatment with the composition of the invention.
Figure 4:
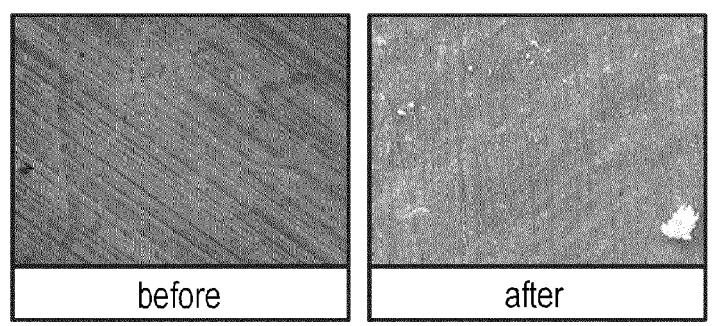
FIG. 4: Topographic SEM image of the untreated (0 d) and treated (14 d) dentin surface.

Following complete disintegration of the coating, two effects can be observed (FIGS. 3, 4).

FIG. 3 shows dentin surfaces with vertical dentinal tubules before (0 d) and after (14 d) the treatment with the composition of the invention. In FIG. 3 it is apparent that the dentinal tubules are completely closed, in comparison to the untreated surface.

In FIG. 4 it is evident that the unevennesses and defects on the dentin surface have been significantly minimized as a result of the treatment. FIG. 4 shows a topographic SEM image of the untreated (0 d) and treated (14 d) dentin surface.

Figure 5:
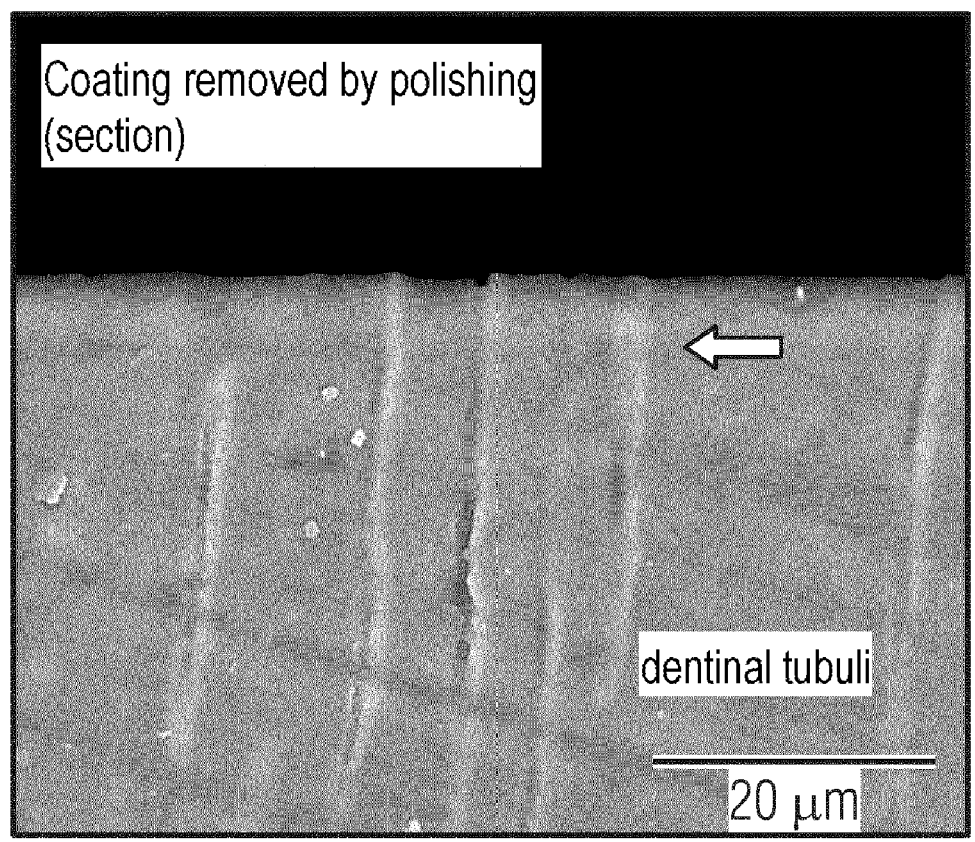
FIG. 5: Cross section through dentinal tubuli in a dentin surface treated with the composition of the invention after 14 d (top in the image).

When a transverse section relative to the dentinal tubules is prepared (FIG. 5), the sealing of the tubules as a result of the treatment with the bioglass-based remineralizing paste is clearly evident.

The invention claimed is:

1. A composition for remineralizing teeth, comprising:
a) calcium phosphate (CaP) glass, and
b) aqueous silica ($SiO_2$) sol;
wherein the composition comprises $SiO_2$ sol 30-35% w/w, water 60-70% w/w, and CaP glass 2-3% w/w, based on the total amount of the $SiO_2$ sol, water and CaP glass constituents, wherein the $SiO_2$ sol contains 10-90% by mass $SiO_2$ and the remainder water.

2. The composition as claimed in claim 1, wherein the CaP glass is ground and sieved and has a particle size <100 μm.

3. The composition as claimed in claim 2, wherein the particle size of the CaP glass has a $D_{50}$<35 μm and/or a $D_{90}$<90 μm.

4. The composition as claimed in claim 1, further comprising fully demineralized water and dilute hydrochloric acid, wherein the dilute hydrochloric acid is prepared from 1.62 g of 35% hydrochloric acid per 100 g of fully demineralized water.

5. The composition as claimed in claim 1, further comprising chlorhexidine digluconate.

6. The composition as claimed in claim 1, wherein the calcium phosphate glass is produced of equimolar amounts of $CaCO_3$ and $P_2O_5$.

7. A method for remineralizing teeth, the method comprising contacting a tooth neck with the composition as claimed in claim 1.

* * * * *